United States Patent [19]

Kelman

[11] 4,056,855
[45] Nov. 8, 1977

[54] INTRAOCULAR LENS AND METHOD OF IMPLANTING SAME

[76] Inventor: Charles Kelman, 150 E. 58th St., New York, N.Y. 10022

[21] Appl. No.: 674,392

[22] Filed: Apr. 7, 1976

[51] Int. Cl.² .......................... A61F 1/16; A61F 1/24
[52] U.S. Cl. ........................................ 3/13; 128/24 A
[58] Field of Search .............. 3/13, 1; 128/24 A, 305, 128/303 R

[56] References Cited

U.S. PATENT DOCUMENTS

| | | | |
|---|---|---|---|
| 3,693,613 | 9/1972 | Kelman | 128/24 A |
| 3,866,249 | 2/1975 | Flom | 3/13 |
| 3,902,495 | 9/1975 | Weiss et al. | 128/24 A |
| 3,925,825 | 12/1975 | Richards et al. | 3/13 |
| 3,991,426 | 11/1976 | Flom et al. | 3/13 |

*Primary Examiner*—Ronald L. Frinks
*Attorney, Agent, or Firm*—Kane, Dalsimer, Kane, Sullivan & Kurucz

[57] ABSTRACT

An intraocular lens and the method of its implantation through an incision in the eye. The assembly includes a lens member and a supporting wire initially in disassembled condition and adapted to be introduced independently through a small incision in the eye. The supporting wire has a base portion which is adapted to fit and be mounted behind the iris of the eye, and has a pair of resilient legs projecting from the pupil, forward of the iris which are adapted to receive a lens therebetween snapped into position by resiliently parting the legs while both components are located in the eye and thereby assembling and mounting the intraocular lens in position in the anterior portion of the eye for use.

4 Claims, 7 Drawing Figures

U.S. Patent Nov. 8, 1977 Sheet 1 of 3 4,056,855
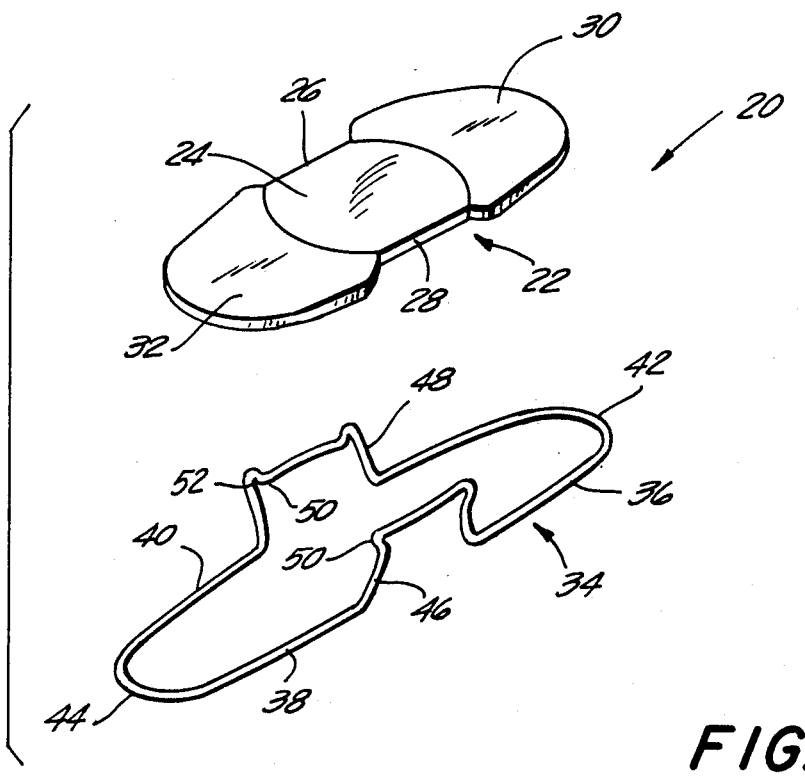
FIG. 1
FIG. 6
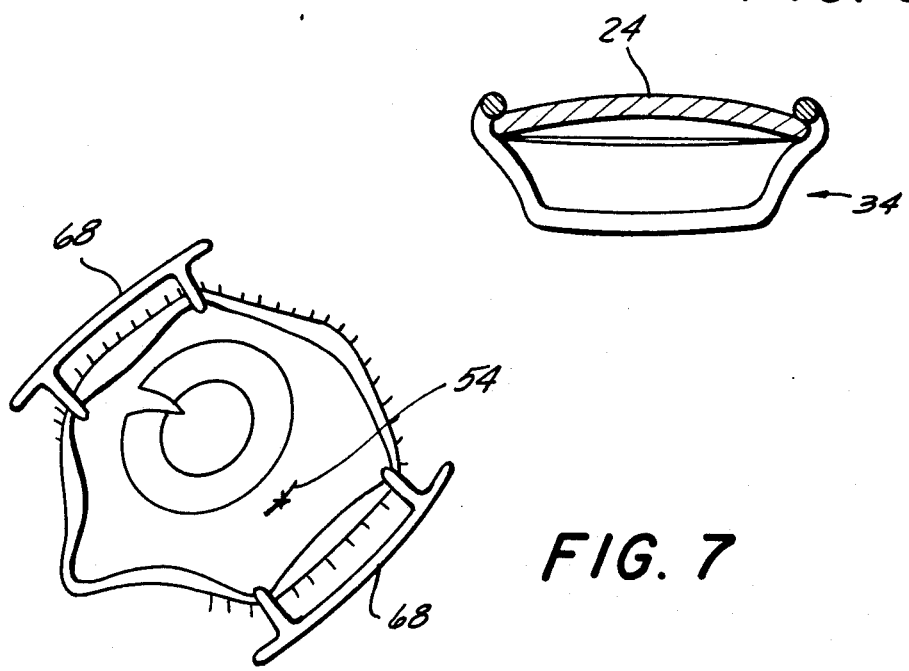
FIG. 7

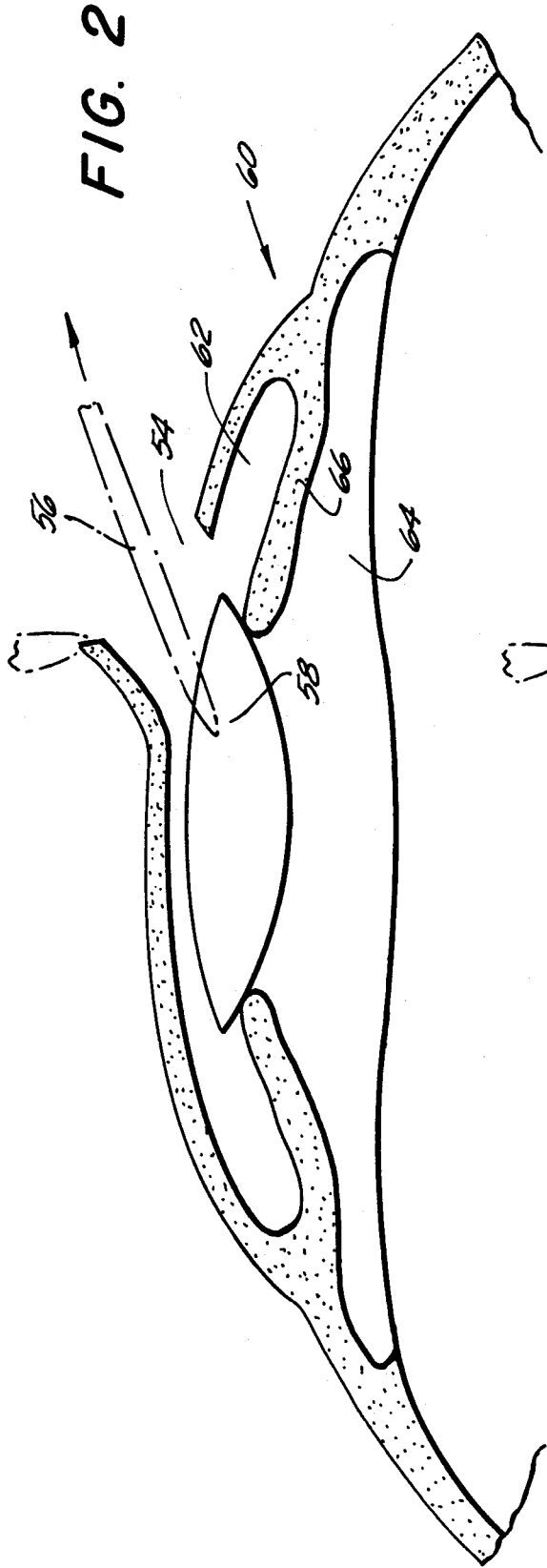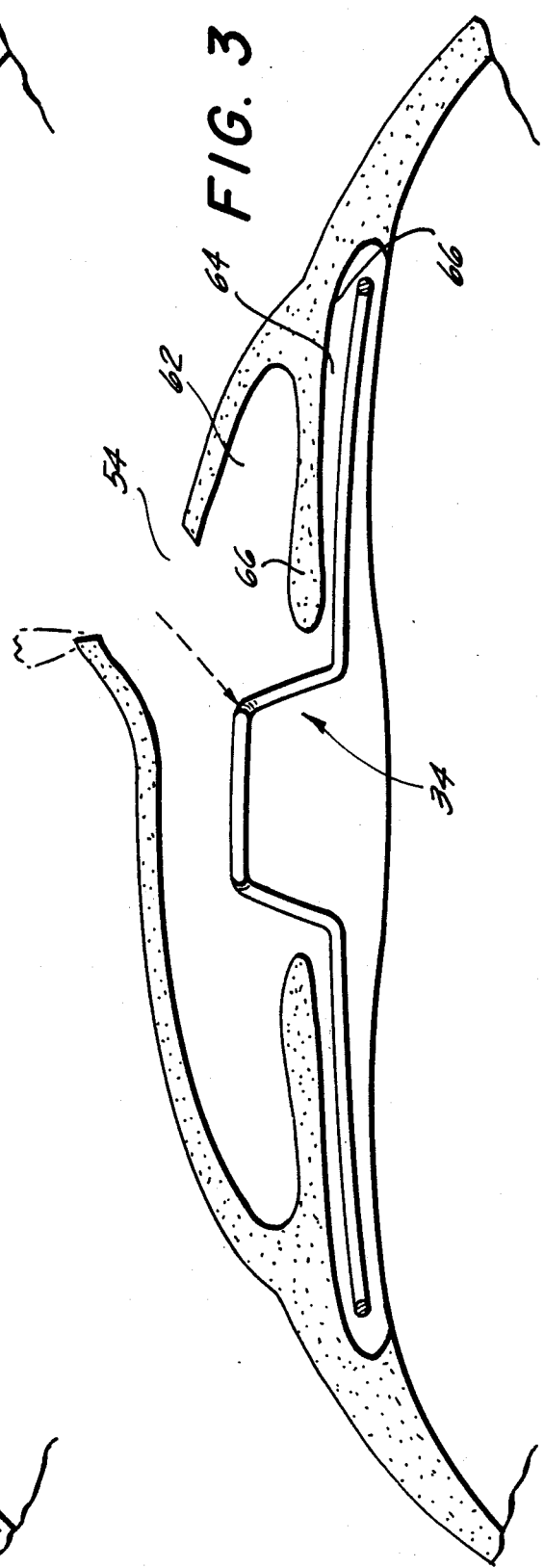

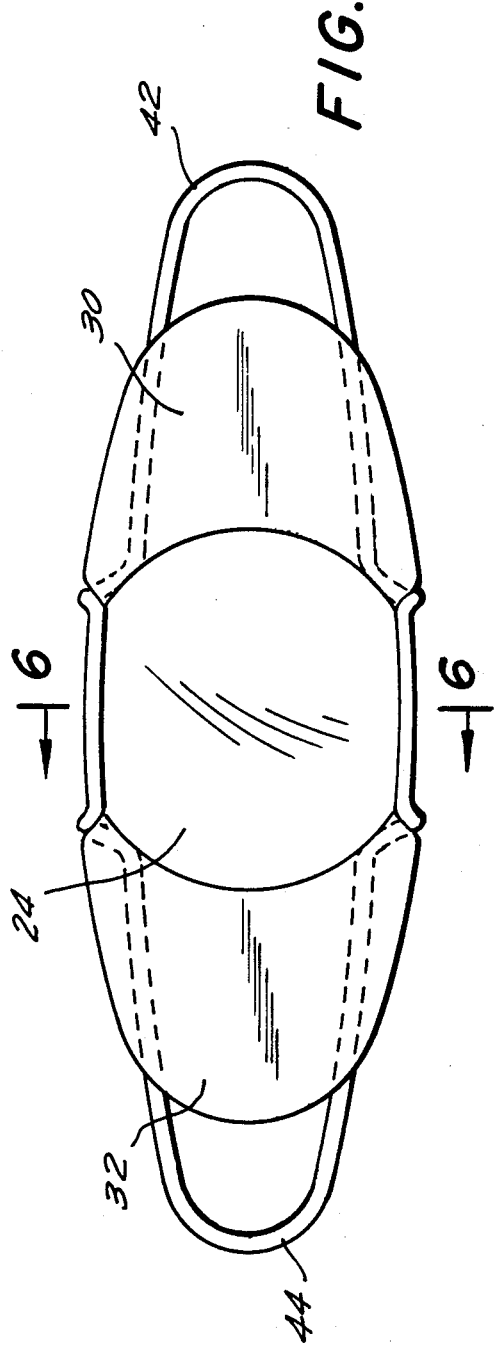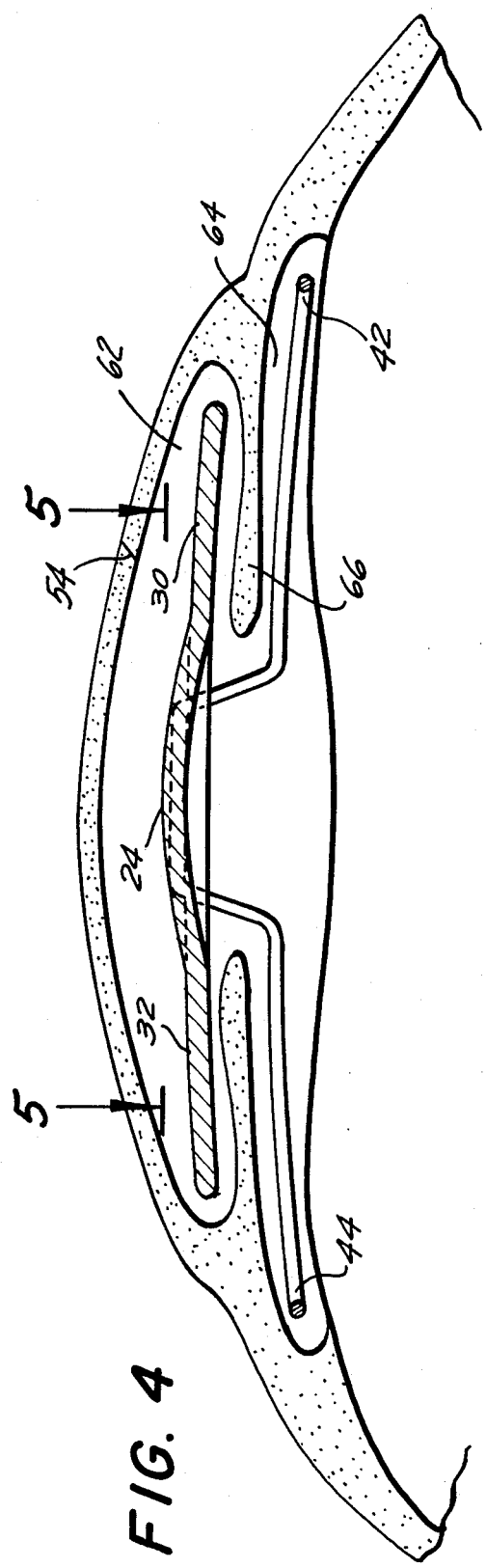

INTRAOCULAR LENS AND METHOD OF IMPLANTING SAME

BACKGROUND OF THE INVENTION

In the history of oprthalmic surgery the problem of cataract removal has been a constant concern and surgical techniques have progressed through the years to improve the effectiveness of cataract removal and to lessen the pain and discomfort for the patient. Naturally if cataracts are permitted to remain in the eye they cause blurred vision and eventual blindness.

Cataracts were once removed with forceps through a 180 degree incision which was uncomfortable for the patient and required a long recovery period of many weeks. The same is true for the cryogenic probe procedure which is used by many surgeons today. This procedure also requires a very large incision.

After the cataract is removed it is under certain conditions an advisable procedure to insert an artificial lens and mount the lens in the eye. With the large incision this caused no extreme difficulty for the surgeon since the assembled lens and supporting structure can be passed through the large incision and mounted in the eye in conventional fashion, such as by engagement with surrounding eye tissue or by suturing the supporting structure in position.

I have developed a unique procedure for removal of cataracts which has proved to be an extremely advantageous over either of the two above discussed techniques. By use of an ultrasonic drill I am able to dissolve, emulsify and remove a cataract through a two or three millimeter incision. The instrument finally perfected utilizes a sharp-tipped drill, vibrating at 40,000 strokes per second. With each miniature tap, the drill's tip dissolves a minuscule fragment of the lens, which is simultaneously sucked away by a pump. No longer is it necessary to provide an incision of 180°, a small two or three millimeter incision is sufficient for permitting the shock tip drill to reach the proper location within the eye.

The result is a much faster procedure, causing less patient discomfort, and permitting the patient to return to ordinary activity much sooner. My patients resume their normal lives the day following the operation, whereas, after the traditional operation, the patient convalesces for up to 6 weeks.

My technique requires a single suture that remains permanently and harmlessly in the eye of the patient. The standard technique requires six to eight stitches. The operation is performed under a microscope. After the incision is made, the tiny drill is inserted into the chamber that separates the cornea from the lens. When the drill makes contact with the lens, it is automatically activated and begins dissolving and sucking out the cataract. Depending upon the age of the patient, the entire drilling process entends no longer than from under a minute to five minutes.

Naturally with only a 2 millimeter incision, it is more difficult to insert an intraocular lens through the incision to mount it in the eye after the cataract operation is completed. Accordingly, there is obviously room for improvement in the types of intraocular lenses manufactured for use and also in the technique for mounting the lenses in the eye.

SUMMARY OF THE INVENTION

With the above background in mind, it is among the primary objectives of the present invention to provide an intraocular lens which is initially formed of two separate components. The two components can be inserted independently through the small incision into the eye with one component, the supporting component mounted in position in the eye and then assembled within the eye to the other component which is the actual lens component. In this manner, by permitting the intraocular lens to be introduced into the eye in disassembled form and then assembled in the eye, the problems associated with previously mounting irregularly shaped intraocular lenses within the eye through a small incision after a cataract operation is overcome.

In summary, the intraocular lens adapted to be implanted in the eye includes a lens member and a support wire having a predetermined configuration so as to have surfaces thereon for mounting the wire in the eye and surfaces thereon for securing the lens member in coupled interengagement therewith. The technique is to initially insert the separate lens member and support wire independently into the eye and than assemble them in position mounted in the eye.

Naturally, the insertion and assembly can be effectively accomplished under the microscope as is utilized in my cataract operation procedures. The principal problem being overcome is the ability to introduce the lens assembly into the eye through the very small incision and thereby not having to enlarge the incision and cause the resultant problems discussed above that occur with a large incision.

With the above objectives in mind among others, references is had to the attached drawings.

BRIEF DESCRIPTION OF THE DRAWINGS

In The Drawings:

FIG. 1 is an exploded view of the intraocular lens assembly of the invention;

FIG. 2 is an enlarged sectional view of the eye showing an ultrasonic drill tip in phantom being used to remove a cataract;

FIG. 3 is a sectional view thereof after the cataract has been removed and with the support wire of the lens assembly having been positioned in the eye;

FIG. 4 is a sectional view of the assembled intraocular lens assembly mounted in the eye and the incision having been closed;

FIG. 5 is a sectional top view thereof taken along the plane of line 5—5 of FIG. 4;

FIG. 6 is a sectional end elevation view thereof taken along the plane of line 6—6 of FIG. 5;

FIG. 7 is a plan view of an eye showing clamps holding the tissue surrounding the eye apart and showing the small suture required to close the small incicion in the eye.

DESCRIPTION OF THE PREFERRED EMBODIMENT

FIG. 1 shows the intraocular lens 20 in disassembled form. The assembly includes a lens member 22 which has an annular shaped central lens portion 24 with the exception of two opposed flat edges 26 and 28. Extending from the curved sides of lens portion 24 are a pair of curved tongue portions 30 and 32 to thereby provide an overall elongated elliptically shaped lens member 22.

The central lens portion 24 is curved slightly to provide the necessary optical path for light. For material, it has been found that plexiglass or other similar plastic operates effectively for lens member 22 and the thickness of the lens member is in the range approximating 0.2 millimeters. The length of the lens member 22 is approximately 6 to 8 millimeters and the width of the lens ranges between approximately 2 and 4 millimeters. These dimensions are approximate and are given only to show the relatively small size of the lens structure. The lens size varies according to the patient.

The other portion of intraocular lens assembly 20 is the support wire 34 which includes a base 36 having two elongated opposing sides 38 and 40 integrally formed with a pair of curved opposing end portions 42 and 44 to form a continuous elongated loop.

Intermediate the longer sides 38 and 40 are a pair of opposed upstanding U-shaped legs 46 and 48 which are integrally formed with legs 38 and 40 respectively. The U-shaped upstanding legs terminate in hook like curved flanges 50 which extend inwardly and downwardly toward one another. The flanges form arcuate recesses 52 which are used to capture the flat sides 26 and 28 of lens 22 as shown in FIG. 6. The actual assembly is accomplished by forcing the lens into position by displacing legs 46 and 48 away from one another until the sides 26 and 28 of lens 22 can snap into position in the arcuate recesses 52 as shown in FIG. 6. The tendency of the resilient legs 46 and 48 of the wire to return to its initial configuration exerts sufficient force on the lens to hold it in fixed position with respect to the support wire thereby completing the assembly.

The material used for wire 34 must have sufficient resilience and be acceptable for use for permanent installation in a human eye. It has been found that platinum is adequate for this purpose and naturally there are other conventional well known substitutes for this material which also satisfy the requirements for the support wire. In overall size it is comparable to the lens 22 and is somewhat longer approximating 8 to 10 millimeters in length and is narrower so that displacement of opposing upstanding U-shaped legs can occur to snap the lens 22 into fixed position in coupled relationship therewith. A platinum-iridium wire of 0.15 millimeters has been found to function effectively for the present assembly. Once again, the size is variable and is dependent on a number of well known parameters including patient eye size.

In operation of the present technique, the previously described technique for cataract removal which I have previously developed should be taken into consideration. Turning to FIG. 2, it can be seen how a small incision 54 can be made in the outer wall of the eye to permit introduction of an ultrasonic drill 56 for interengagement with a cataract 58 formed on the lens portion of the eye 60. The eye is divided into an anterior chamber or capsule 62 and a posterial chamber or capsule 64. Separating the two chambers is the iris 66. After the cataract has been withdrawn from the eye in the direction shown by the arrow in FIG. 2 the support wire 34 is inserted through the same small incision 54 in an easy and effective manner. Since the wire is only approximately of 0.15 millimeters thickness it can be easily threaded through a very small incision. The wire is then positioned with its longer curved ends 42 and 44 extending well into the posterior portion 64 of the eye. In this position they are closely surrounded by tissue 66 within the eye which will adhere to the base portions closely adjacent thereto and fix the wire 34 in position. Naturally, if the amount of tissue is not sufficient at this point or there is some question, a small suture can be employed to affix the ends 42 and 44 to the surrounding tissue 66 of the eye. Extending through the opening where the cataract has been removed into the anterior portion 62 as shown in FIG. 3 are two upstanding opposing legs 46 and 48 in position for receipt of lens member 22.

Lens member 22 is then threaded through the small incision 54 and is snapped into position in coupled relationship with legs 46 and 48 with edges 26 and 28 mounted in recesses 52 formed by flanges 50. As discussed above, the flanges are slightly separated away from one another a further amount than the normal position so as to engage and hold the lens in position. This configuration and arrangement is depicted in FIGS. 4 and 5. It can be seen in FIGS. 4, 5 and 7 how the small incision 54 has been easily closed with a single suture. In FIG. 7 it is also depicted how a pair of opposed clamps 68 are utilized to hold the tissue surrounding the eye away from the operating area of the eye during the procedures involved in removing the cataract, inserting the components of assembly 20, assembling these components in the eye, and then closing the small incision 54.

The end of the portions of the base loop are bent slightly backward and lie behind the optic portion and are inserted into the capsule bag. Because they are in intimate contact with tissues of the inner eye they are made of 0.15 millimeter platinum-irridium, a most inert alloy. The weight of the implant is of no consequence and is easily tolerated with capsular fixation. Naturally the actual size of the lens assembly is a matter of choice depending upon the size of the eye one is working on. This is true for both the support wire and the lens.

For fixation, it is helpful to have a relatively strong capsular membrane behind the iris. Whereas the central area of the membrane consisting of the posterior lens capsule only should be clear as possible, it is adviseable to leave some cortical remnants of the lens at the periphery. This promotes the development of capsular adhesions imbedding parts of the wire loops of the base portion and giving extra stability. Naturally as suggested above, if capsule fixation is not possible or acceptable, suture can be employed to fix the wire in position.

The sequence of introduction of components and steps of assembled can be varied, if it is so desired. For example, the lens can be inserted first and then the support wire. Also, it is possible to assemble the lens to the support wire before affixing the support wire in the eye.

Thus the several aforenoted objects and advantages are most effectively attained. Although several somewhat preferred embodiments have been disclosed and described in detail herein, it should be understood that this invention is in no sense limited thereby and its scope is to be determined by that ot the appended claims.

I claim:

1. A method of implanting an intraocular lens through an incision in the eye comprising; introducing a supporting wire of predetermined shape and a separate lens through the incision and placing the wire in position for use and coupling the lens with the wire within the eye, the lens being inserted through a small incision made in the eye for purposes of removal of a cataract, the supporting wire being in the form of an elongated loop with a pair of integral aligned supporting legs extending upwardly from the central portion of the opposed longer sides of the loop, each leg terminating in an inward arcuate flange, the supporting wire being a resilient material and configured so that when it is inserted in the eye and the elongated end portions extending from the central portion are positioned in the posterior portion of the eye and fixed in position, the legs will extend upwardly into the anterior portion of the eye beyond the iris, the lens being elliptical in configuration and being coupled with the wire by resiliently separating the legs from one another and permitting the lens to snap into position underneath the curved flanges with the legs attempting to return to the relaxed configuration toward one another holding the lens in position in the anterior portion of the eye.

2. The invention in accordance with claim 1 wherein the legs of the wire are sutured in position to the surrounding tissue of the posterior portion of the eye.

3. An intraocular lens adapted to be implanted in the eye comprising; a lens member, a support wire having a predetermined configuration so as to have surfaces thereon for mounting the wire in the eye and surfaces thereon for receiving the lens member in coupled interengagement therewith after the wire is mounted in the eye, the supporting wire being resilient and including an elongated loop forming a base and having a pair of upstanding integral aligned legs extending intermediate the ends of the longer sides of the base, each leg terminating in an inwardly extending arcuate flange to form a recess therebetween, the lens being substantially elliptical in configuration and being slightly larger than the distance between the legs of the supporting wire when in relaxed position to that upon application of sufficient pressure to separate the resilient legs of the supporting wire away from one another the lens can be snapped into position in the recesses formed by the opposing flanges on the legs whereby a release of the legs and their tendency to return to the relaxed configuration will engage and hold the lens in position, the base being extendable into the posterior portion of the eye to be held in fixed position therein and in turn permitting the legs to extend into the anterior portion of the eye and hold the interengaged lens in position for use in the eye.

4. The invention in accordance with claim 3 wherein the end portions of the base are adapted to be sutured into fixed position with respect to the surrounding tissue portions of the eye when mounted in the desired position in the posterior portion thereof.

* * * * *